US00PP18098P2

(12) United States Plant Patent
Heffron et al.

(10) Patent No.: US PP18,098 P2
(45) Date of Patent: Sep. 25, 2007

(54) ***IMPATIENS* PLANT NAMED 'BALFAFPINSAR'**

(50) Latin Name: *Impatiens×hybrida*
Varietal Denomination: Balfafpinsar

(75) Inventors: Leslie Heffron, Santa Maria, CA (US); Tau-San Chou, Batavia, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/296,818

(22) Filed: Dec. 7, 2005

(51) Int. Cl.
*A01H 5/00* (2006.01)

(52) U.S. Cl. ..... Plt./317

(58) Field of Classification Search ..... Plt./317
See application file for complete search history.

*Primary Examiner*—Kent Bell
*Assistant Examiner*—S. B. McCormick-Ewoldt
(74) *Attorney, Agent, or Firm*—Audrey Charles

(57) ABSTRACT

A new and distinct cultivar of *Impatiens* plant named 'Balfafpinsar' characterized by its pink-colored flowers with lavender edges, dark green-colored foliage, and vigorous, trailing growth habit.

1 Drawing Sheet

Latin name of genus and species of plant claimed: *Impatiens×hybrida.*
Variety denomination: 'Balfafpinsar'.

BACKGROUND OF THE INVENTION

The present invention relates to a new and distinct cultivar of *Impatiens* plant botanically known as *Impatiens×hybrida* and hereinafter referred to by the cultivar name 'Balfafpinsar'.

The new cultivar originated in a controlled breeding program in Illinois during November 2002. The objective of the breeding program was the development of *Impatiens* cultivars with numerous large flowers, attractive flower colors, and trailing, freely basal branching growth habit.

The new cultivar is an irradiation induced sport of 'Balfaforg', U.S. Plant Pat. No. 14,690, characterized by its orange-colored flowers, dark green-colored foliage, and semi-trailing growth habit. The irradiation occurred on Nov. 5, 2002. The new cultivar was discovered and selected on May 27, 2003 in a controlled environment at Arroyo Grande, Calif.

Asexual reproduction of the new cultivar by terminal stem cuttings since May 2003 at Arroyo Grande, Calif. and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balfafpinsar' as a new and distinct cultivar of *Impatiens* plant:

1. Pink-colored flowers with lavender edges;
2. Dark green-colored foliage; and
3. Vigorous, trailing growth habit.

Plants of the new cultivar differ from plants of the parent primarily in flower color.

Of the many commercially available *Impatiens* cultivars known to the inventors, the most similar in comparison to the new cultivar is 'Balfaflav', not patented. However, in side by side comparisons, plants of the new cultivar differ from plants of 'Balfaflav' in the following characteristic: Plants of the new cultivar have a different flower color from plants of 'Balfaflav'.

In addition, the new cultivar is similar in comparison to 'Balfafbricol', co-pending U.S. Plant patent application Ser. No. 11/296,803. However, in side by side comparisons, plants of the new cultivar differ from plants of 'Balfafbricol' in mature foliage color and fully-open petal color.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balfafpinsar'. The plants were grown in 10 cm pots for 9 weeks in a greenhouse at West Chicago, Ill.

DETAILED BOTANICAL DESCRIPTION

Figure 1:
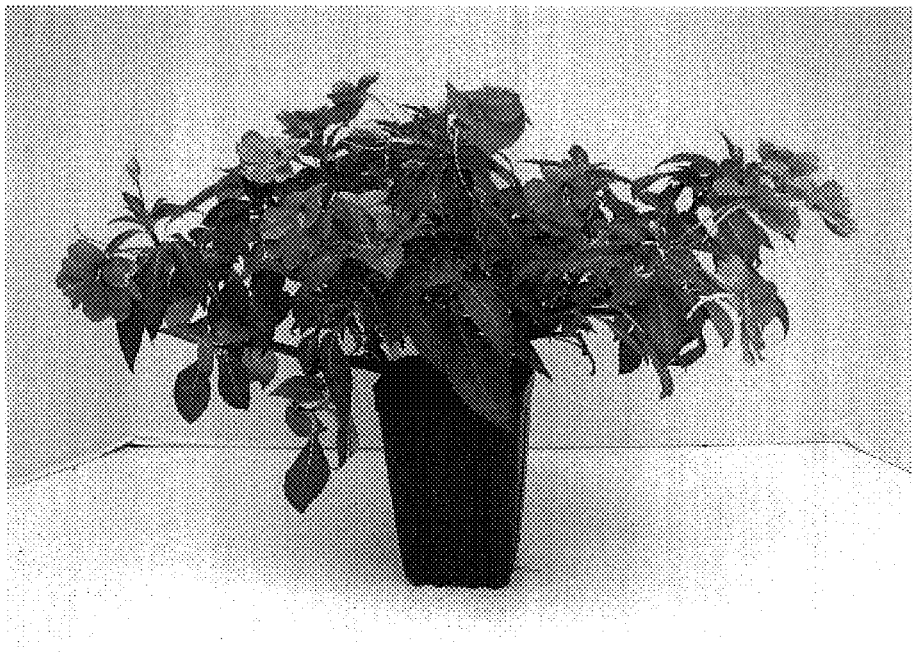
FIG. 1 illustrates a side view of the overall growth and flowering habit of 'Balfafpinsar'.
Figure 2:
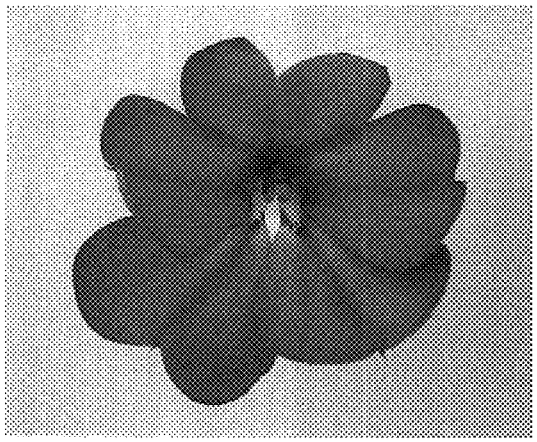
FIG. 2 illustrates a close-up view of a first open individual flower of 'Balfafpinsar'.
Figure 3:
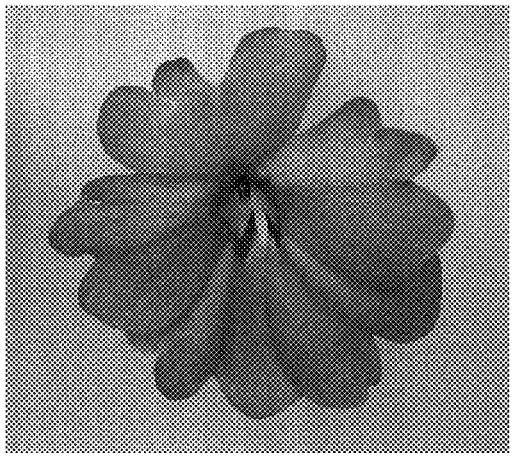
FIG. 3 illustrates a close-up view of a fully mature individual flower of 'Balfafpinsar'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Jul. 30, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 9 weeks utilizing a soilless growth medium. Greenhouse temperatures were maintained at approximately 68° F. to 80° F. (20° C. to 26° C.) during the day and approximately 60° F. to 65° F. (15° C. to 18° C.) during the night. Greenhouse light levels of 4,000 to 7,000 footcandles were maintained during the day.

Botanical classification: *Impatiens×hybrida* cultivar Balfafpinsar.

Parentage:

*Parent.*—'Balfaforg', U.S. Plant Pat. No. 14,690.

Propagation:

*Type cutting.*—Terminal stem.

*Time to initiate roots.*—Approximately 7 to 8 days.

*Time to produce a rooted cutting.*—Approximately 21 to 28 days.

*Root description.*—Fine and fibrous.

*Rooting habit.*—Freely branching.

Plant description:

*Crop time.*—Approximately 6 to 8 weeks from a rooted cutting.

*Growth habit and general appearance.*—Vigorous, trailing.

*Size.*—Height from soil level to top of plant plane: Approximately 20.4 cm. Width: Approximately 52.2 cm.

*Branching habit.*—Freely basal branching. Approximately 5 branches per plant.

*Branch.*—Strength: Strong. Length: Approximately 20.6 cm. Diameter: Approximately 9.0 mm. Texture: Pubescent. Color: 145B with overlay of 187B. Internode length at center of branch: Approximately 3.3 cm.

*Foliage.*—Number of leaves per main branch: Approximately 14. Fragrance: None. Form: Simple. Arrangement: Alternate. Aspect: Petiole is at acute angle to stem: leaf blade is perpendicular to stem. Shape: Elliptic. Margin: Serrate, ciliate. Apex: Acuminate. Base: Attenuate. Venation pattern: Pinnate. Length of leaf at center of stem: Approximately 6.0 cm. Width of leaf at center of stem: Approximately 2.6 cm. Texture of upper surface: Glabrous. Texture of lower surface: Glabrous with puberulent midvein. Color of upper surface of mature foliage: Closest to 139A with venation of 143C. Color of lower surface of mature foliage: Closest to 138A with venation of 137A. Petiole length: Approximately 1.3 cm. Petiole diameter: Approximately 2.1 mm. Petiole texture: Glabrous. Petiole color: 145D.

Flowering description:

*Flowering habit.*—'Balfafpinsar' is freely flowering under outdoor growing conditions with substantially continuous blooming from spring through autumn and year round in greenhouse environment.

*Time to first flower.*—Approximately 12 weeks from sticking of unrooted cutting.

*Lastingness of individual bloom.*—Approximately 6 to 7 days.

Flower description:

*Type.*—Single. Borne: Above foliage. Quantity per plant at 9 weeks: Approximately 12. Fragrance: None.

*Bud rate of opening.*—Generally takes 4 to 5 days for bud to progress from first color to fully open flower.

*Bud just before opening.*—Shape: Ovate. Quantity showing color at any one time: 7. Length: Approximately 1.5 cm. Diameter: Approximately 8.2 mm. Color: Closest to N66C.

*Corolla.*—Shape: Round, slightly cupped when first open, petals become flattened with age. Diameter: Approximately 5.1 cm. Depth: Approximately 1.2 cm.

*Petals.*—Quantity: 5. Shape: Obovate. Aspect: Slightly cupped when first open, petals become flattened with age. Appearance: Iridescent. Margin: Entire. Apex: Emarginate. Base of upper petal: Truncate. Base of lateral and lower petals: Attenuate with each lateral petal fused with a lower petal at base. Texture: Glabrous. Length of upper petal: Approximately 2.2 cm. Width of upper petal: Approximately 3.2 cm. Length of lateral petal: Approximately 2.7 cm. Width of lateral petal: Approximately 2.3 cm. Length of lower petal: Approximately 3.3 cm. Width of lower petal: Approximately 2.7 cm. Color of upper surface of upper and lateral petals when first open: 58C with 58B along midrib and varying amounts of N78B along margin. Color of upper surface of lower petals when first open: 58C with 58B along midrib, varying amounts of N78B along margin, and area of 61C just above the base of N155B. Color of lower surface of all petals when first open: 55C. Color of upper surface of upper and lateral petals when fully open: 52B with 52A along midrib, varying amounts of N78B along margin, and 61C at base. Color of upper surface of lower petals when fully open: 52B with 52A along midrib and area of 61A just above the base of N155B. Color of lower surface of all petals when fully open: 55C.

*Spur.*—Quantity: One per flower. Length: Approximately 5.5 cm. Diameter at tip: Approximately 0.8 mm. Diameter at base: Approximately 2.1 mm. Texture: Glabrous. Color: 145C with tip of 145B.

*Peduncle.*—Strength: Strong. Aspect: Slightly acute angle to stem. Length: Approximately 4.9 cm. Diameter: Approximately 3.6 mm. Texture: Glabrous. Color: 145B.

*Calyx.*—Quantity of sepals per flower: 4; upper sepal is fused to lower surface of upper petal. Apex: Acuminate. Texture of upper and lower surfaces: Glabrous. Shape of lateral sepal: Ovate. Length of lateral sepal: Approximately 1.2 cm. Width of lateral sepal: Approximately 6.3 mm. Color of upper surface of lateral sepal: Closest to N144D. Color of lower surface of lateral sepal: 144D. Shape of lower sepal: Ovate. Length of lower sepal: Approximately 1.5 cm. Width of lower sepal: Approximately 1.1 cm. Color of lower sepal: 155C at base with overlay at margin of N74C and tip of 143C.

*Reproductive organs.*—Androecium: Stamen quantity: 5, fused around pistil at apex. Anther shape: Hooded. Anther length: Approximately 2.0 mm. Anther color: N155B. Pollen amount: Abundant. Pollen color: 4D. Gynoecium: Pistil quantity: One per flower. Pistil length: Approximately 4.5 mm. Stigma shape: Five pointed star. Stigma length: Approximately 0.3 mm.

Stigma color: Colorless, translucent. Style length: Approximately 1.1 mm. Style color: 144D. Ovary length: Approximately 3.1 mm. Ovary diameter: Approximately 1.8 mm. Ovary texture: Glabrous. Ovary color: 143C.

Seed and fruit production: Neither seed nor fruit production has been observed.

Disease and pest resistance: Resistance to pathogens and pests common to *Impatiens* has not been observed.

What is claimed is:

1. A new and distinct cultivar of *Impatiens* plant named 'Balfafpinsar', substantially as herein shown and described.

* * * * *